(12) United States Patent
Keltjens et al.

(10) Patent No.: US 6,717,015 B2
(45) Date of Patent: Apr. 6, 2004

(54) VENLAFAXINE BESYLATE

(75) Inventors: Rolf Keltjens, Nijmegen (NL); Johannes Jan Platteeuw, s'Hertogenbosch (NL); Juan Cucala Escoi, Barcelona (ES); Inocencia Margallo Lana, Barcelona (ES); Frantisek Picha, Brno (CZ); Montserrat Gallego Luengo, Barcelona (ES)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 10/397,373

(22) Filed: Mar. 27, 2003

(65) Prior Publication Data

US 2003/0195249 A1 Oct. 16, 2003

Related U.S. Application Data

(60) Provisional application No. 60/427,181, filed on Nov. 19, 2002, and provisional application No. 60/367,734, filed on Mar. 28, 2002.

(51) Int. Cl.$^7$ .................. C07C 215/42; A01N 33/02; A61K 31/135
(52) U.S. Cl. .................. 564/355; 564/360; 514/653
(58) Field of Search ................ 564/355, 360; 514/653

(56) References Cited

U.S. PATENT DOCUMENTS

| | | |
|---|---|---|
| 4,535,186 A | 8/1985 | Husbands et al. |
| 5,043,466 A | 8/1991 | Shepard |
| 5,916,923 A | 6/1999 | Rudolph et al. |
| 6,197,828 B1 | 3/2001 | Jerussi et al. |
| 6,274,171 B1 | 8/2001 | Sherman et al. |
| 6,403,120 B1 | 6/2002 | Sherman et al. |
| 6,419,958 B2 | 7/2002 | Sherman et al. |
| 6,444,708 B2 | 9/2002 | Rudolph et al. |
| 2001/0012855 A1 | 8/2001 | Rudolph et al. |
| 2001/0055612 A1 | 12/2001 | Sherman et al. |
| 2002/0006443 A1 | 1/2002 | Curatolo et al. |

FOREIGN PATENT DOCUMENTS

| | | |
|---|---|---|
| CN | 1225356 | 8/1999 |
| CN | 1240206 | 1/2000 |
| EP | 0797991 A1 | 10/1997 |
| WO | WO99/22724 A2 | 5/1999 |
| WO | WO00/32556 A1 | 6/2000 |
| WO | WO00/76955 A1 | 12/2000 |
| WO | WO01/07397 A1 | 2/2001 |
| WO | WO02/45658 A2 | 6/2002 |

OTHER PUBLICATIONS

Database CAPLUS on STN, Acc. No. 1988:461453, Davison et al., DE 3710457 A1, Oct. 8, 1987 (abstract).*

Zhang et al., "Novel Isomerization Reaction of N,N–Dimethyl–α–(methoxycarbonyl)–4–substituted–benzylammonium N–Methylides," J. Org. Chem. vol. 64, 1999, pp. 581–586.

Roberts et al., "Addition of Eschenmoser's salt to Ketone, Ester, & Lactone Enolates. A Convenient Synthesis of α–Methylene Carbonyls Via Mannich Intermediates," Tetrahedron Letters No. 19, 1977, pp. 1621–1624.

S. Jane deSolms, "N,N,N',N'–Tetramethylmethanediamine. A Simple, Effective Mannich Reagent," J. Org. Chem. vol. 41, No. 15, 1976, pp. 2650–2651.

Yardley, et al., "2–Phenyl–2–(1–dydroxycycloalkyl) ethylamine Derivatives: Synthesis and Antidepressant Activity," J. Med. Chem., vol. 33, 1990, pp. 2899–2905.

Makhija et al., "Once Daily Sustained Release Tablets of Venlafaxine, A Novel Antidepressant," European Journal of Pharmaceutics and Biopharmaceutics, vol. 54, 2002, pp. 9–15.

Nenitzescu et al., "The Syntheis of Cyclic Alcohols and Olefins by the Interaction of Dimagnesium Halides and Esters," The Laboratory of Organic Chemistry, Scoala Politehnica, 1950, pp. 3483–3486.

* cited by examiner

Primary Examiner—Brian Davis
(74) Attorney, Agent, or Firm—Mark R. Buscher

(57) ABSTRACT

Venlafaxine besylate compounds provide certain advantages over venlafaxine hydrochloride and are useful in forming pharmaceutical compositions and n treating venlafaxine-treatable diseases and conditions. Venlafaxine besylate can be easily formulated into an extended release dosage form including a hydrogel tablet as well as other matrix-based tablet compositions. A preferred tablet making process involves hot melt granulation.

49 Claims, No Drawings

VENLAFAXINE BESYLATE

This application claims the benefit of priority under 35 U.S.C. §119 from prior U.S. provisional patent application Ser. No. 60/427,181 filed Nov. 19, 2002 and from prior U.S. provisional patent application Ser. No. 60/367,734 filed Mar. 28, 2002, the entire contents of both provisional applications being incorporated herein by reference.

BACKGROUND OF THE INVENTION

The present invention relates to a novel acid addition salt of venlafaxine, namely venlafaxine besylate, various forms thereof, and the use of the same in pharmaceutical compositions for treating depression and other conditions.

Venlafaxine is the common name for the compound 1-[2-(dimethylamino)-1-(4-metboxyphenyl) ethyl] cyclohexanol, having the structure shown below.

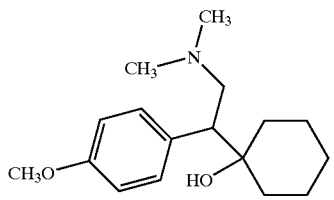

U.S. Pat. No. 4,535,186 describes a class of hydroxycycloalkanephenethyl amines as being useful antidepressants and exemplifies the compound now known as venlafaxine hydrochloride as one of the suitable species. Venlafaxine hydrochloride is approved for sale in various countries including the United States of America. It is available as an immediate release tablet and as an extended release capsule, under the brand name EFFEXOR® (Wyeth Ayerst) and EFFEXOR XR® (Wyeth Ayerst), respectively.

Venlafaxine has been the subject of various research endeavors. For example, U.S. Pat. No. 5,043,466 describes a process for making cyclohexanol derivatives in a specified solvent composition. Example 3 of this patent shows the synthesis of venlafaxine as the hydrochloride salt thereof.

U.S. Pat. No. 6,274,171 and related EP 0 797 991A1 disclose encapsulated extended release formulations for venlafaxine hydrochloride. These patents indicate that commercial venlafaxine hydrochloride tablets were administered two or three times daily, but that due to variations in the drug concentration in the patient's blood plasma caused by such a dosing regimen, unwanted side effects, especially nausea and vomiting were common. A once daily, encapsulated extended release dosage form is disclosed that provides a flattened drug plasma profile and reduces these side effects. The encapsulated dosage form is taught to comprise spheroids of venlafaxine hydrochloride, microcrystalline cellulose, and hydroxypropylmethylcellulose (HPMC). These spheroids are coated with a mixture of ethyl cellulose and HPMC. By providing an appropriate amount of the coating, the desired blood plasma profile can be obtained. An acceptable batch of coated spheroids will meet the following in vitro dissolution profile:

| Time (hours) | Average % venlafaxine hydrochloride released |
| --- | --- |
| 2 | <30 |
| 4 | 30–55 |
| 8 | 55–80 |
| 12 | 65–90 |
| 24 | >80 | using USP Apparatus 1 (basket) at 100 rpm in purified water at 37° C. The coated spheroids can be from a single batch or represent a blend of batches having different dissolution profiles.

U.S. Pat. No. 6,274,171 and EP 0 797 991 also state that forming an extended release dosage form of venlafaxine hydrochloride was difficult in part due to the high water solubility of the hydrochloride salt. In fact, these patents disclose that "[n]umerous attempts to produce extended release tablets by hydrogel technology proved to be fruitless because the compressed tablets were either physically unstable (poor compressibility or capping problems) or dissolved too rapidly in dissolution studies." See U.S. Pat. No. 6,274,171 at column 4, lines 60–65 and EP 0 797 991A1 at page 3 lines 35–37. Unlike the encapsulated extended release formulations described in these patents, a hydrogel extended release venlafaxine hydrochloride tablet is taught to typically exhibit a dissolution profile wherein 40%–50% is released at 2 hours, 60%–70% is released at 4 hours, and 85%–100% is released at 8 hours.

WO 99/22724 also discloses encapsulated venlafaxine hydrochloride extended release dosage forms. These formulations differ from those in U.S. Pat. No. 6,274,171 and EP 0 797 991A1 in that the spheroid is substantially free of HPMC. Apparently HPMC can be omitted from the spheroid when smaller amounts of venlafaxine hydrochloride are employed.

U.S. Pat. No. 6,197,828 and WO00/32556 disclose the use of individual (+) and (−) enantiomers, respectively, of venlafaxine as well as metabolites thereof. While the commercial venlafaxine hydrochloride is a racemate, these patents teach that various side effects may be reduced by using one isomer substantially without the presence of the other.

Although venlafaxine hydrochloride provides good pharmaceutical activity, it would be beneficial to find other forms of venlafaxine. In particular, venlafaxine forms that are easier to handle would be advantageous. Venlafaxine hydrochloride is relatively aggressive towards handling equipment and is irritating to the skin, etc. of human personnel that handle the pure active. A venlafaxine form that is less aggressive and less irritating would be desirable. It is further desirable to provide a venlafaxine form that can be easily formulated into various dosage forms including hydrogel extended release tablets.

SUMMARY OF THE INVENTION

The present invention is based on the discovery of a new form of venlafaxine, namely venlafaxine besylate. Accordingly, a first aspect of the invention relates to a venlafaxine besylate compound. The compound can be isolated and/or purified or it can be part of a composition. The compound can be in solid form including crystalline forms but is not limited thereto. A preferred compound is crystalline venlafaxine besylate monohydrate.

Another aspect of the present invention relates to a pharmaceutical composition comprising an effective amount of venlafaxine besylate and a pharmaceutically acceptable excipient. The composition can be an immediate release dosage form or an extended release dosage form and embraces tablets as well as pellets/beads/spheroids or other encapsulated forms. In one embodiment, the venlafaxine besylate is provided in a hydrogel tablet. The hydrogel tablet preferably provides sufficient extended release so that the tablet is a once daily dosage form. In another preferred embodiment, the extended release composition uses a lipophilic matrix and is conveniently made by a hot melt granulation technique.

A further aspect of the invention relates to the use of venlafaxine besylate in treating venlafaxine-treatable diseases or conditions and/or in making medicaments for treating such diseases or conditions. Hence the invention provides a method for treating a venlafaxine-treatable disease or condition, which comprises administering to a patient in need thereof an effective amount of venlafaxine besylate. The venlafaxine besylate is typically administered as an oral composition such as a tablet or capsule and is preferably administered once daily.

Another aspect of the present invention relates to a process of making a venlafaxine besylate formulation that comprises mixing venlafaxine besylate and a molten fusible carrier to form a partially melted mass; and cooling the partially melted mass to form a solidified product. The solidified product is typically a granulate and can be converted to a tablet or pellet.

DETAILED DESCRIPTION OF THE INVENTION

The present invention is based on the surprising discovery that venlafaxine besylate, i.e. venlafaxine benzenesulfonate, has advantageous properties in comparison to venlafaxine hydrochloride. First, venlafaxine besylate is much less water soluble than venlafaxine hydrochloride. For example, venlafaxine besylate monohydrate exhibits a solubility of about 25 mg/ml in water and less than 30 mg/ml in 0.1 N HCl at ambient conditions. In contrast, venlafaxine hydrochloride exhibits a water solubility of about 570 mg/ml at ambient conditions. This reduced solubility can be advantageous in formulating an extended release dosage form. In addition, venlafaxine besylate is less aggressive, less irritating, and easier to handle than venlafaxine hydrochloride. The besylate salt can be formed into a powder that is less irritating to the personnel handling the material than the hydrochloride salt and that can be readily transported by mechanical apparatus and compressed into a tablet. Generally, venlafaxine besylate powder has a higher bulk density and a higher tapped density (e.g., 500 tap) than venlafaxine hydrochloride. Additionally, venlafaxine besylate has a relatively lower melting point which can be advantageous in certain formulating techniques such as hot melt granulation and molecular dispersions, particularly in combination with lipophilic excipients. Accordingly, venlafaxine besylate is easier to formulate into a variety of dosage forms, especially extended release dosage forms, than venlafaxine hydrochloride.

A venlafaxine besylate compound is any form of the salt formed by venlafaxine and benzene sulfonic acid. The venlafaxine in the venlafaxine besylate compound of the present invention can be any form of venlafaxine. For example, venlafaxine has one optically active carbon, thus allowing for existence of two enantiomers and a racemate. Both enantiomers are pharmaceutically active. The venlafaxine besylate compound can be based on the racemate or mixture of enantiomers of venlafaxine, which is preferred, or on the pure or substantially pure (+) or (−) enantiomer of venlafaxine (hereinafter referred to as (+)-venlafaxine besylate and (−)-venlafaxine besylate): all are included in within the meaning of "venlafaxine besylate" unless specifically noted otherwise. The compound can be in isolated and/or purified form, but such is not required. The compound includes various physical forms of the salt including dissolved forms, oil or liquid forms, and solid forms including amorphous and crystalline forms.

The compound is typically in a crystalline form. Crystalline forms include venlafaxine besylate anhydrates, hydrates, and solvates. Preferably the venlafaxine besylate is venlafaxine besylate monohydrate or venlafaxine besylate anhydrate. The monohydrate generally has a melting range around 100° C. such as about 85–114° C. and a DSC peak around 114° C. Surprisingly, the (+)- or (−)-venlafaxine besylate anhydrate are each less hygroscopic than the racemate version of venlafaxine besylate anhydrate.

A venlafaxine besylate compound can be prepared by contacting a venlafaxine substrate with a benzenesulfonate substrate. Typically the contacting occurs in a suitable solvent system. The venlafaxine besylate product can be isolated, if desired, by precipitation, evaporation, spray drying, or other conventional techniques known in the art.

The "venlafaxine substrate" includes any substance that provides a venlafaxine moiety or ion thereof and specifically includes, in racemic or enantiomeric form, venlafaxine base, a venlafaxine salt other than venlafaxine besylate (e.g. venlafaxine HCl) and a raw venlafaxine, i.e. a reaction product or reaction mixture comprising venlafaxine that has been obtained after the last step of production of venlafaxine. The venlafaxine substrate can be obtained by conventional processes and synthesis schemes known in the art. For example, U.S. Pat. No. 4,535,186, U.S. Pat. No. 5,043,466, and U.S. Pat. No. 6,197,828 all teach methods for making venlafaxine. Venlafaxine base in its isolated state is obtainable by neutralization of venlafaxine hydrochloride, extraction by ethyl acetate and evaporation of the solvent, according to the method disclosed in U.S. Pat. No. 6,197,828 and WO 00-32566. Alternatively, venlafaxine base can be obtained as a precipitate without the need to convert to a salt, preferably as a filtratable precipitate. Precipitation of venlafaxine free base can be achieved by the use of a contrasolvent, e.g. heptane, optionally with cooling and/or solvent removal, as is more fully described in provisional patent application No. 60/367,736, filed Mar. 28, 2002, entitled "Venlafaxine Free Base," the entire contents of which are incorporated herein by reference. Single enantiomers of venlafaxine free base can be made as described in J. Med. Chem. 1990, 33 (10), 2899–2905. Venlafaxine hydrochloride is commercially available and can be produced according to U.S. Pat. No. 4,535,186, EP 112669, U.S. Pat. No. 5,043,466, U.S. Pat. No. 6,197,828 and WO 01-07397. Other salts can be formed by methods analogous to those disclosed in these cited patent documents.

The "benzenesulfonate substrate" includes any substance that provides a benzene sulfonic acid moiety or ion thereof and specifically includes any form of benzene sulfonic acid, such as benzene sulfonic acid or a hydrate thereof, and a salt of benzene sulfonic acid with a base. A preferred substrate is benzene sulfonic acid monohydrate. Benzenesulfonate substrates including benzene sulfonic acid, its hydrates and/or salts thereof are commercially available and/or may be prepared by methods known in the art.

The molar ratio of the substrates is not particularly limited and is generally about stoichiometric; i.e. molar ratio of venlafaxine substrate to benzenesulfonate substrate within the range of 0.8:1 to 1.2:1, more typically 0.9:1 to 1.1:1 or about 1:1. However, up to a significant excess of one substrate, especially the benzenesulfonate substrate can be used. Such excess of either benzenesulfonate or venlafaxine is typically in the range of 1.1 to 3.0:1, more typically 1.1 to 2:1. For economy reasons, excesses are normally kept small and typically the excess benzenesulfonate substrate, if any, is provided in slight stoichiometric excess such as 1.1 to 1.5 times the molar amount of venlafaxine.

The solvent system is preferably selected so as to facilitate the salt reaction and to allow subsequent separation of the resulting besylate. Advantageously, both venlafaxine substrate and the benzenesulfonate substrate are dissolvable, at least partly, in the solvent system, at least at elevated temperatures. In the process, a mixture, slurry, or solution of venlafaxine substrate and a solvent may be contacted with a benzenesulfonate substrate, or conversely, a mixture, slurry, or solution of benzenesulfonate substrate and a solvent may be contacted with venlafaxine substrate. In another embodiment, both partners may be combined with a solvent system prior to being contacted together, whereby the solvent system used for benzenesulfonate substrate may be identical with or different from the solvent system used for the venlafaxine substrate. The solvent system can be comprised of a single solvent or a mixture of solvents. When two or more solvents are used, a two phase reaction scheme may be used wherein the venlafaxine substrate and benzenesulfonate substrate are primarily reacted in one phase and the resulting venlafaxine besylate compound is primarily present in the other phase due to, inter alia, solubility differences, etc. Suitable solvents include water, a lower alcohol ($C_1$–$C_6$) such as methanol or ethanol, an aliphatic ketone such as acetone, an ether such as dioxane, an ester such as ethyl acetate, and mixtures thereof. Preferred solvents are methanol and acetone.

The temperature of contact of both substrates in the solvent system is from ambient to the boiling point of the solvent system, with elevated temperatures, but generally less than the boiling point, being preferred. It is not required that a complete solution is formed in this step, i.e. a slurry or two phase solution are also possible, though a single solution is generally preferred.

The venlafaxine besylate compound can be isolated or recovered from the salt forming reaction by any convenient means. For example, the venlafaxine besylate compound can be precipitated out of a solution or reaction mixture. The precipitation may be spontaneous depending upon the solvent system used and the conditions. Alternatively, the precipitation can be induced by reducing the temperature of the solvent, especially if the initial temperature at contact is elevated. The precipitation may also be facilitated by reducing the volume of the solution/solvent or by adding a contra solvent, i.e. a liquid miscible with the solvent in which the venlafaxine besylate is less soluble. Seed crystals of venlafaxine besylate may also be added to help induce precipitation. The precipitated venlafaxine besylate compound can be isolated by conventional methods such as filtration or centrifugation, optionally washed and dried, preferably under diminished pressure.

Alternatively, the venlafaxine besylate compound can be isolated by evaporating away the solvent and collecting the residue. Such a method generally leads to an oil or solid amorphous form of venlafaxine besylate. Similarly, an amorphous solid form of the venlafaxine besylate compound can be recovered by spray drying a solution containing the venlafaxine besylate compound.

Venlafaxine besylate prepared in solid state may be, if necessary, purified to the desired degree of purity. Venlafaxine besylate can be purified for instance by a (re) crystallization from a suitable solvent that may be identical or different from the solvent system used for its production. Examples of preferred suitable solvents for a purifying crystallization step are acetone, ethanol, water, ethyl acetate, methanol, isopropanol, chloroform, and combinations thereof. The crystallization can be carried out by any known technique such as those described above for precipitating venlafaxine besylate. Generally, the addition of seed crystals is advantageous as is the use of a contrasolvent to facilitate or enhance the crystallization.

In a preferred embodiment, venlafaxine besylate monohydrate is formed. In general, a crystalline monohydrate can be formed by precipitating the venlafaxine besylate in the presence of water. The presence of essentially stoichiometric amounts of water is generally all that is necessary for the precipitation to form the monohydrate. The use of less water can result in partial hydration. The use of excess water could result in greater hydration, although the monohydrate is the most easily formed hydrate. The water may be present in or added to the solvent system or it may originate from any of the substrates, especially in the benzenesulfonate substrate.

In a preferred mode, (+/–)-venlafaxine base is dissolved in acetone under heating, benzene sulfonic acid monohydrate is added to the solution under stirring, the mixture is heated to complete dissolution and the clear solution is allowed to cool. Racemic venlafaxine besylate monohydrate crystallizes from the solution and is separated by filtration and dried.

When the venlafaxine substrate is another salt of venlafaxine, water can be advantageously used as the solvent system or as part of the solvent system in forming a hydrate. For instance, racemic venlafaxine hydrochloride can be dissolved in water, benzene sulfonic acid (or an aqueous solution of benzene sulfonic acid) can be added thereto, and the mixture stirred, preferably at ambient temperature, until the venlafaxine besylate salt starts to precipitate. The mixture is generally held under optional cooling until precipitation is complete, e.g. 1–3 hours. The solid is isolated by filtration. After drying, the racemic venlafaxine besylate is obtained as a monohydrate.

Anhydrous venlafaxine besylate may be essentially prepared as disclosed above, provided however that water is not present. Alternatively, anhydrous venlafaxine besylate may be prepared by dehydration of venlafaxine besylate hydrate. The dehydration methods may comprise conventional drying, preferably at elevated temperatures and/or in vacuo, but a more preferred mode is azeotropic drying. This process comprise mixing venlafaxine besylate hydrate with a solvent that forms an azeotrope with water, heating the mixture to the boiling point and distilling off the azeotropic mixture water-solvent. A preferred solvent for this method is toluene.

Anhydrous (+/–)-venlafaxine besylate is a hygroscopic compound and it may absorb water until a content corresponding to monohydrate (approximately 4% by weight) is obtained. Complete water (re)uptake can occur, e.g., after storage of anhydrous venlafaxine besylate at 40° C./75% RH for 3 days. (+/–)-Venlafaxine besylate monohydrate, either prepared as above or obtained by (re)uptake of water, is however substantially non-hygroscopic.

The dehydration/rehydration process can be an advantageous mode to prepare venlafaxine besylate monohydrate in small crystals of uniform particle size. The principle has been described earlier for ondansetron hydrochloride dihydrate (see EP 415 522), and is applicable for venlafaxine besylate. Specifically, a venlafaxine besylate monohydrate is dehydrated which causes the crystal lattice to contract or shrink. Upon rehydration, the lattice generally does not expand. Thus cycling from monohydrate to dehydrate to monohydrate results in a stable but smaller particle size form of the original venlafaxine besylate monohydrate. The process may replace conventional milling, whenever necessary, in preparing the active for making a pharmaceutical formulation. However, such a process is generally not suitable for (+)- or (−)-venlafaxine besylate as the anhydrate form is significantly less hygroscopic than the (+/−)-venlafaxine anhydrate.

Single enantiomers of venlafaxine besylate may be prepared essentially as disclosed above, whereby the venlafaxine substrate comprises the single enantiomer of venlafaxine. Preferred substrates are single enantiomers of venlafaxine base or venlafaxine hydrochloride.

The most preferred venlafaxine besylate compound is racemic venlafaxine besylate monohydrate. In solid state, racemic venlafaxine besylate monohydrate is typically a solid microcrystalline product that visually melts, under release of water, at around 100° C. A melting endotherm of an essentially pure compound, recorded by a DSC (10° C./min), occurs at around 114° C. The DSC performed at low heating rate (1° C./min) sometimes shows an additional endotherm at about 100° C. indicating the release of water before final melt. The same may be observed during visual observation of melting by microscope.

In purified state, it has substantially white color. The solid form of racemic venlafaxine besylate monohydrate is generally in powder form having an average particle size of 100 microns or less. Such a powder form can be obtained by precipitation, dehydration/rehydration and/or by milling a solid form or mass.

The venlafaxine besylate compound of the present invention can be formulated with a pharmaceutically acceptable excipient into a pharmaceutical composition. The pharmaceutical compositions of the present invention include the unit dosage form as well as the intermediate bulk formulations such as pellets, beads, granules, powder blends, etc. Typically the composition is a finished dosage form also referred to as a unit dose. Dosage forms include oral dosage forms, topical dosage forms such as a transdermal patch, parenteral dosage forms such as an injectable solution, and rectal dosage forms such as a suppository, but is not limited thereto. Oral dosage forms are the most preferred due to the ease of administration and include solid oral dosage forms such as capsules, tablets, sachets/granules, and powders, as well as liquid oral dosage forms such as solutions, suspensions, and emulsions.

Pharmaceutically acceptable excipients are well known in the art and include diluents, fillers, binders, lubricants, disintegrants, glidants, colorants, pigments, taste masking agents, sweeteners, plasticizers, and any acceptable auxiliary substances such as absorption enhancers, penetration enhancers, surfactants, co-surfactants, and specialized oils. The proper excipient(s) are selected based in part on the dosage form, the intended mode of administration, the intended release rate, and manufacturing reliability. Examples of common types of excipients include various polymers, waxes, calcium phosphates, and sugars. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethyleneoxides; and polyacrylic acids including their copolymers and crosslinked polymers thereof, i.e. Carbopol® (B.F. Goodrich), Eudragit® (Rohm), polycarbophil and chitosan polymers. Waxes include white beeswax, microcrystalline wax, carnauba wax, hydrogenated castor oil, glyceryl behenate, glycerylpalmito stearate, saturated polyglycolyzed glycerate. Calcium phosphates include dibasic calcium phosphate, anhydrous dibasic calcium phosphate, and tribasic calcium phosphate. Sugars include simple sugars such as lactose, maltose, mannitol, fructose, sorbitol, sacarose, xylitol, isomaltose, and glucose as well as complex sugars (polysaccharides) such as maltodextrin, amylodextrin, starches, and modified starches.

Any form of the venlafaxine besylate can be used in the pharmaceutical composition. Preferred venlafaxine besylate forms are: crystalline (+/−)-venlafaxine besylate monohydrate, (+)-venlafaxine besylate monohydrate, (−)-venlafaxine besylate monohydrate, (+)-venlafaxine besylate anhydrate, and (−)-venlafaxine besylate anhydrate. The amount of venlafaxine besylate compound contained in a unit dosage form is an amount effective to treat one or more venlafaxine-treatable diseases or conditions as is hereinafter defined and can be determined by workers skilled in the art without undue experimentation. Generally this amount ranges from 2 mg to 300 mg. For oral dosage forms the amount is generally from 30 mg to 300 mg per unit dose. Contemplated doses include amounts of about 37.5 mg, 75 mg, 100 mg, 112.5 mg, 150 mg, 200 mg, and 300 mg strengths. For clarity, all amounts of venlafaxine besylate are expressed herein in terms of the weight of the free base contained in the venlafaxine besylate compound, as is conventional in the art.

As mentioned above, oral dosage forms are preferred and include tablets, or capsules/sachets filled with granules or powders. Tablets can be soluble tablets, dispersible tablets, effervescent tablets, chewable tablets, lyophilized tablets, bi-layer or multi-layer tablets, coated tablets including sugar coatings, enteric coatings, and gastro-soluble coatings, and modified release tablets including microencapsulated active substance tablets, matrix tablets, and coated tablets such as polymer coated extended release tablets and osmotic tablets of the mono-compartmental or bi-compartmental type. Capsules include hard gelatin capsules that can be filled with powder, pellets, granules, small tablets or mini-tablets. The capsule and/or the material placed within can be coated such as for enteric release or modified release. Soft capsules are also included and are more typically filled with liquids or dispersions, but are not limited thereto. The sachets are alternative dosage forms to capsules. The material filled into capsules or sachets may be optionally suitably treated: e.g. the granules can be effervescent granules, coated granules, enteric granules, or modified release granules.

One embodiment of the present invention relates to an immediate release tablet. An "immediate release" as used herein means that at least 80% of the venlafaxine besylate in the tablet is dissolved by 30 minutes under a dissolution test using USP Apparatus 1 (basket) at 100 rpm in purified water at 37° C. Any conventional immediate release composition can be used in formulating the venlafaxine besylate immediate release tablet. Typically such tablets contain one or more binders and/or diluents such as HPMC, microcrystalline cellulose, a calcium phosphate, lactose, and mannitol; a lubricant such as magnesium stearate; and optionally a disintegrant such as sodium starch glycollate, crosscarmellose or crosspovidone. Additional excipients such as colorants, antioxidants, etc can also be present.

More preferably, however, the solid oral dosage form is an extended release dosage form. This can be accomplished in either a tablet or a capsule form. An extended release dosage form as used herein means that in a dissolution test using USP Apparatus 1 (basket) at 100 rpm in purified water at 37° C., less than 80% of the venlafaxine besylate is dissolved during the first two hours, more typically less than 50%, and preferably less than 30% of the venlafaxine besylate is dissolved during the first two hours. Extended release tablets or capsules generally allow for twice a day, or more preferably once a day dosing, to provide 24 hour therapeutic blood plasma levels of venlafaxine to the patient. In this regard, the most preferred dosage form is one which provides once daily dosing. Such a composition should meet the following in vitro dissolution profile:

| Time (hours) | Average % venlafaxine besylate released |
|---|---|
| 2 | <30 |
| 4 | 30–55 |
| 8 | 55–80 |
| 12 | 65–90 |
| 24 | >80 | using USP Apparatus 1 (basket) at 100 rpm in purified water at 37° C. Preferably, an extended release dosage form meets the above dissolution profile using a two media dissolution test. Specifically, during the first two hours, the media is a simulated gastric fluid (SGF) of pH 1.2 while during the remaining hours the media is a simulated intestinal fluid (SIF) of pH 6.8. This two media test can provide more accurate predictions of in vivo performance in some circumstances, especially when an enteric coating is present on the dosage form. Most advantageously the extended release dosage form meets the above dissolution profile in both 0.1 N HCl aqueous solution as well as pure water.

For purposes of the present invention, the simulated fluids are defined as follows:

SGF (USP Simulated Gastric Fluid without pepsin) composition:

| HCl | qs | pH 1.2 |
|---|---|---|
| NaCl | | 0.2% |
| water | qs | 1000 ml |

SIF (USP Simulated Intestinal Fluid without pancreatin) composition:

| $KH_2PO_4$ | | 6.8 g |
|---|---|---|
| NaOH | qs | pH 6.8 |
| water | qs | 1000 ml |

In terms of in vivo performance, the extended release venlafaxine besylate pharmaceutical composition according to the present invention preferably exhibits on average a maximum venlafaxine blood plasma level not earlier than 4 hours, more preferably not earlier than 6 hours after administration of the composition. Typically the average peak plasma level is reached between 4 and 10 hours, more preferably between 6 and 8 hours after administration. In this regard, a preferred composition is bioequivalent to the commercially available EFFEXOR XR®.

Extended release tablets can be formulated according to any of the known techniques such as those based on matrix technology, osmotic pressure technology, multiparticulates compressed into tablets, multilayer tablets having at least one layer based on one of the foregoing, as well as coated tablets, using known materials and methods.

Tablets employing a matrix, in either a monolithic tablet or in one or more layers optionally built on a tablet core, are generally the most common and frequently the easiest to form from a commercial manufacturing standpoint. The matrix provides a diffusion and/or erosion release of the drug. The matrix is generally composed of at least one type of matrix material selected from hydrophilic (hydrogel), inert, lipophilic, and biodegradable matrix materials. Materials used for each of these kinds of matrices in pharmaceutical oral dosage forms are well known in the art and are briefly described below.

A hydrophilic matrix material is generally a polymeric material that swells upon contact with water to form a diffusion barrier. Suitable materials include cellulose derivatives such as methylcelluloses (i.e. having a viscosity of 400 cP to 4000 cP), hydroxyethylcellulose, HPMC, and sodium carboxymethyl cellulose; polysaccharides such as galactomannanes, potassium alginates, sodium alginates, agar-agar, carrageen, arabic gum, and sterculia gum; polyacrylates such as CARBOPOL 934, EUDRAGIT LD 35; Noveon or polycarbophils; and other water swellable polymers such as polyvinyl alcohol.

Inert matrix materials provide a tortuous path for the drug to escape the dosage form thereby controlling diffusion of the drug. Such materials include ethylcellulose (ETHOCEL).

Lipophilic matrix materials work through erosion and/or diffusion. Examples of lipophilic materials include glyceryl palmitosterate (PRECIROL ATO 5), glyceryl behenate (COMPRITOL 888 ATO) and Hydrogenated castor oil (CUTINA HR).

Biodegradable matrix materials also operate through a combination of erosion and diffusion. Biodegradable materials include, for example, polyesters of lactic acid and glycolic acid, polyorthoesters, polyanhydrides and caprolactones. A further description of this technology is set forth in WO02/11701, WO92/04013, and EP 1 005 863.

Because venlafaxine besylate has a surprisingly lower water solubility than venlafaxine hydrochloride, venlafaxine besylate can be more readily formulated into conventional extended release forms including hydrogel tablets. Surprisingly, venlafaxine besylate can even be formulated into a once-a-day extended release hydrogel tablet. A "hydrogel tablet" is one that contains a hydrophilic matrix material that swells or "gels" upon contact with water to thereby slow the diffusion release of the active ingredient. Any of the above-described hydrophilic matrix materials can be used in forming venlafaxine besylate hydrogel tablets of the present invention.

Preferably a hydrogel tablet of the present invention comprises 10%–50% of a venlafaxine besylate compound, preferably a monohydrate form, and 30% to 75% of a hydrogel-forming agent, preferably an HPMC. In some embodiments it may be advantageous for the weight ratio of venlafaxine besylate to hydrogel-forming agent to be in the range of 0.8–1.2:1, preferably approximately 1:1, respectively. In addition to the venlafaxine besylate and hydrogel-forming agent, the composition may further comprise other suitable inert ingredients such as fillers and lubricants in order to assure good properties of the composition in the process of making final medicinal forms, particularly for compression into tablets. Suitable fillers are, e.g. calcium hydrogenphosphate, microcrystalline cellulose or lactose, suitable lubricants are magnesium stearate, glyceryl palmitostearate, sodium stearyl fumarate (Pruv) or talc.

The relatively low water solubility and relatively low melting point of venlafaxine besylate also affords the formation of an effective extended release dosage form using a lipophilic matrix. A lipophilic matrix is one that contains a lipophilic excipient and forms an inert porous matrix through which the drug dissolves. Preferably a lipophilic matrix-based tablet is formed by hot melt granulation techniques, as is described in more detail hereinafter, wherein the lipophilic matrix material is a fusible carrier. Any of the above identified lipophilic matrix materials can be used as a fusible carrier in a hot melt granulation. The lipophilic matrix-based tablets generally contain 10% to 80% venlafaxine besylate and 5% to 50%, more typically 8% to 30% of the lipophilic matrix material. In some embodiments it is preferable to have a weight ratio of venlafaxine besylate to lipophilic matrix material within the range of 1:0.05–0.7, more preferably approximately 1:0.2, respectively. In addition to the lipophilic matrix material, the tablet can further contain additional suitable excipients as described above. Typically the tablet will contain a filler such as calcium phosphate, microcrystalline cellulose, and/or lactose and a lubricant such as magnesium stearate or talc, but is not limited to these excipients. In some embodiments, especially where granulates containing at least the lipophilic matrix and venlafaxine besylate are used, the tablet can contain wax such as glyceryl behenate, glyceryl palmitostearate or hydrogenated castor oil as a filler. Such extragranulate wax can also assist in avoiding an initial fast dissolution release. The tablet can be enteric film coated in order to avoid the active substance from being released to the stomach, or film coated with some polymer in order to decrease the initial fast release typical of matrix-based tablets. Another option for controlling/limiting the release of the venlafaxine besylate into the gastric fluid is to make an enteric coating with a pore forming agent therein. The tablets based on lipophilic matrix materials are preferably once daily dose tablets.

The tablets of venlafaxine besylate according to the present invention can be made by any known tabletting technique. Suitable techniques include direct compression, dry granulation, wet granulation and hot melt granulation. The tabletting methods that do not employ a solvent ("dry processes") are generally preferable.

In general, dry granulation procedures comprise mixing the solid excipients (except lubricants), compacting the mixture in a compactor (e.g. a roller compactor), or double compression, milling the compacted mass, screening the milled granules, mixing with a lubricant and compressing the mixture into tablets. Direct compression procedures generally comprise mixing the solid excipients in one or more stages and compressing the uniform mixture into tablets. After tablet formation, the tablets may optionally be coated.

In addition to wet and dry granulation, hot melt granulation is also suitable for making venlafaxine besylate pharmaceutical compositions. Hot melt granulation generally comprises mixing a fusible carrier in a molten state with venlafaxine besylate to form a partially melted mass and then cooling the mass to form a solidified product. A fusible carrier is any material that can serve as a binder, carrier or matrix having a melting point within the range of 35° C. to 250° C. Preferably the fusible carrier is lipophilic, i.e., a lipophilic matrix material, and has a melting point within the range of 50° C. to 150° C.

Typically venlafaxine besylate, fusible carrier, and optionally one or more fillers, antiadherent agents, lubricants, etc. are combined or mixed in a granulator. The materials are then heated by any convenient technique, such as by a heating jacket, microwaves, infrared, etc. or a combination of two or more techniques. The mixture is heated to a temperature near or above the melting or softening point of the fusible carrier, thereby allowing the fusible carrier to act as a liquid binder. If two or more fusible carriers are present, such as two lipophilic matrix forming materials, the temperature need only reach near or above the melting or softening point for one of the carriers. This state is considered a "molten" state for purposes of the present invention. The venlafaxine besylate does not have to melt during this heating or mixing step. The molten fusible carrier is mixed with the venlafaxine besylate and any additional optionally combined excipients to form a partially melted mass. Preferably the mixing is sufficient, given the degree of melting/fluid state of the carrier, the relative amounts of the carrier, the venlafaxine besylate, and any other excipients present, to form a substantially uniform mixture of the combined ingredients. The mixing is preferably carried out using an impeller and a chopper (stirring blades). While the ingredients are normally combined in a non-molten state and mixed before as well as during the heating step, such is not required. For example, the fusible carrier in molten state can be directly combined and mixed with the venlafaxine besylate. Similarly, the mixing may begin only after the fusible carrier starts to soften, partially melt, or completely liquefy.

Once mixed into the desired partially melted mass, the mass is cooled to form a solidified product. The cooling can be passive, i.e. by removing the heat source, but more typically involves applying a cooling technique such as cool water through a jacket surrounding the granulation bowl and/or with gas transmission through the bowl mass. The solidified product can be in the form a granules or larger in size such as pellets. Alternatively, the solidified product may comprise much larger pieces such that milling is required to obtain powder or granules. The partially melted mass is preferably also mixed during the cooling step. As in the first mixing step, the mixing preferably is carried out in a granulator using an impeller and a chopper (stirring blades). Mixing during the cooling serves to break up the solidifying mass and aids in the production of granules or pellets.

The solidified product is then converted to a tablet by techniques known in the art. Typically the solidified product is sieved or milled and sieved, optionally combined with one or more additional excipients such as a lubricant and then compressed into tablets. In preferred embodiments, at least the lubricant and more preferably all additional excipients, if any, are mixed with the solidified product to form a tabletting mixture. The tabletting mixture is compressed into tablets. Alternatively, it is possible for all the tablet ingredients to be present in the solidified product.

The tablets made from a hot melt granulation technique are preferably lipophilic matrix-based tablets, more preferably they form extended release tablets as discussed above. In any event, the hot melt granulation tablet preferably has a release profile that satisfies the following:

| Time (hours) | Average % venlafaxine besylate released |
|---|---|
| 2 | <30 |
| 4 | 30–55 |
| 8 | 55–80 |
| 12 | 65–90 |
| 24 | >80 | using USP Apparatus 1 (basket) at 100 rpm in purified water at 37° C. Most preferably the tablets are once daily dose tablets. The extended release tablets preferably have an enteric or functional coating in order to avoid release of the drug in the stomach or control an otherwise initial fast release. When coated, it is preferred that the extended release tablet satisfies the above dissolution profile in the two media dissolution test described above.

As mentioned above, the venlafaxine besylate tablets of the invention may be coated. Typically the coating provides suitable gastro-resistance to delay the onset of release of the active component from the tablet. Examples of coating material for gastro-resistant coatings are cellulose acetate phthalate (CAP) (Aquacoat CPD™), co-processed polyvinyl acetate phthalate (PVAP) (Suretetic™), cellulose acetate trimellitate (CAT), acrylic-methacrylic acid copolymers (Eudragit type polymers) (Acryl-EZE™), hydroxypropyl methylcellulose phthalate (HP), hydroxypropyl methyl cellulose acetate succinate (HPMCAS). Such an enteric coating is useful in matrix-based tablets because of the tendency of such tablets to have an initial burst effect due to the presence of the active on or near the surface of the tablet. Complete enteric resistance is not required. While any of the tablets can be coated with a gastric-resistant coating, generally the hydrogel tablet is not so coated due to the desire to allow swelling of the matrix. Another technique that can be used to control the initial burst effect is a so-called "bilayer" tablet in which an insoluble layer is coated or placed on one major face of the tablet. This insoluble layer limits the amount of active present on the surface and thereby reduces the initial burst. The insoluble layer, which is normally insoluble in both gastric and intestinal fluid, retards the overall release as the tablet surface area is reduced. Suitable insoluble layer materials include polysiloxanes and ethylcellulose. The insoluble layer can be formed by compression after the tablet is formed. Another technique that can be used to control the initial burst effect is to make an enteric coating that contains a pore forming agent. A pore forming agent is an excipient that is soluble in simulated gastric media. Thus, owing to the dissolution of the pore forming agent from the enteric coating layer, a small quantity of the drug is released in simulated gastric media and then the rest is released in simulated intestinal media. Typical pore forming agents include sugars such as sucrose and are typically added to the enteric coating material in an amount of up to 50%, more typically 5 to 40%, more typically 10 to 30%, and in some embodiments about 20%, by weight.

In addition to gastric resistance, the tablets may be coated for color, taste masking, and/or stability reasons using conventional materials and techniques.

The venlafaxine besylate tablets can be of any size and shape. In one preferred embodiment the tablets are small or mini-tablets in size. Small tablets have a diameter of 3–6 mm while mini-tablets have a diameter of 1–3 mm. One or more of the tablets can be taken as such or, more preferably one or more are loaded into a single capsule to provide a unit dose. Most preferably, the small or mini-tablets provide additive amounts of the venlafaxine besylate without modifying the release profile. For example, by making a hydrogel round small tablet of diameter 5 to 6 mm and containing 37.5 mg of venlafaxine besylate, capsules containing 37.5 mg, 75 mg, and 150 mg of venlafaxine besylate can be formed by filling a standard No. 0 capsule with 1, 2, or 4 of the small tablets, respectively. Such an additive effect is not as easily obtained with a proportionally larger hydrogel tablet. This is because the release is a function of the volume to surface area ratio. Scaling up the amount and size of a satisfactory 37.5 mg tablet will likely not result in a satisfactory release profile for the resulting 150 mg tablet, for example, because the volume to surface area ratio is different between the two tablets. For each desired single dosage level, a separate formulation, size and/or shape would be needed. Similar proportionality issues arise with other delayed release tablet technologies. By using small tablets in a single capsule, only one tablet formulation and shape is needed to produce multiple dosage strengths. Typically a small or mini-tablet contains 5 to 50 mg of venlafaxine besylate, especially 10, 25, 30, 37.5, 40, and 50 mg. Again, for clarity all amounts are expressed in terms of venlafaxine base. Depending on the size of the tablet and the capsule, from 1 to 10 or more small or mini-tablets can be placed in the capsule.

In addition to filling capsules with small or mini-tablets, an extended release capsule can be formed by filling it with more traditional pellets, beads, and/or spheres. Generally the pellet is comprised of a binder or carrier such as hydroxypropyl methylcellulose, microcrystalline cellulose, or both, but is not limited thereto. The pellets can be coated with an extended release coating or composition such as ethyl cellulose, acrylate polymers, hydroxypropyl methylcellulose, or a mixture of two more. In addition, different populations of coated pellets can be used in a single capsule, each providing a different release characteristic so that the aggregate release is sustained over a long period; i.e. 12 to 24 hours. Alternatively, the bead population can be substantially homogeneous. A preferred capsule of the pellet type is described in the above-mentioned U.S. Pat. No. 6,274,171 and related EP 0 797 991 A1 wherein the venlafaxine hydrochloride used in these patents is replaced with the venlafaxine besylate compound of the present invention.

The venlafaxine besylate compound of the present invention can be used to treat any disease or condition that is treatable by venlafaxine. A venlafaxine-treatable disease or condition is one that could be improved by a serotonin or norepinephrine uptake inhibitor and specifically includes, without limitation, depressions, panic disorder, generalized anxiety disorder, obesity, post-traumatic stress disorder, late luteal phase dysphoric disorder, attention deficit disorders, Gilles de la Tourette syndrome, bulimia nervosa, and Shy Drager syndrome. See published U.S. patent application U.S. Ser. No. 2001/0012855 A1 for a description of the uses of venlafaxine and salts thereof. The venlafaxine besylate compound of the present invention can be used to treat such conditions by administering an effective amount to a patient in need thereof. An effective amount is generally known in the art and/or determined using routine skill. Typically the effective amount for a human is 30 to 300 mg of venlafaxine per day. The patients used herein include human and non-human mammals such as dogs, cats, and horses. The route of administration is not particularly limited and includes peroral, parenteral, and transdermal administration. Preferably, the venlafaxine besylate compound is administered orally via one or two unit dosage forms, especially extended release tablets or capsules, as described above.

The entire disclosure in each of the patents and journal articles mentioned in the above description is incorporated herein by reference. The invention will be further described with reference to the following non-limiting examples.

EXAMPLES

In the following examples, racemic venlafaxine, e.g. (+/−)-venlafaxine besylate, is used unless otherwise indicated.

Example 1
Synthesis of Venlafaxine Besylate Monohydrate

In a 1-liter 3-necked flask equipped with a mechanical stirrer and a condenser, 90.0 g of venlafaxine base was dissolved under heating in 140 ml of acetone while stirring under nitrogen atmosphere. Then 52.34 g of benzene sulfonic acid hydrate was added in portions. The resulting mixture was heated into dissolution. The clear solution was allowed to cool to room temperature under stirring. Stirring was continued for 2–3 hours. The obtained crystals were isolated by filtration, washed in two portions of 30 ml of acetone and dried overnight in vacuo at 40° C. Yield: 134.26 g. Water content (Karl-Fischer ): 4% (corresponds to monohydrate). No uptake of water was observed after storage at 40° C. at a relative humidity of 75%. Melting range of around 95–113° C., under loss of water (TGA, DSC).

Example 2A
Venlafaxine Besylate from Venlafaxine Hydrochloride

In a 100 ml flask, equipped with a stirring bar, 2.0 g venlafaxine HCl was dissolved under stirring in 5 ml water. Then, 1.06 g benzene sulfonic acid hydrate was added in one portion dissolved in 3 ml water, and the resulting clear solution was stirred at room temperature for 5 minutes. Then, a trace amount of a previously prepared venlafaxine besylate monohydrate was added. After a few minutes, the crystallization process started. After stirring for an additional 1.5 hours, the solid was isolated by filtration, washed with water and dried at 40° C. overnight at reduced pressure. Isolated yield 2.037 g (70%). According to Karl-Fischer, the water content was 4% corresponding with 1 equivalent (mono-hydrate).

Example 2B

In a 100 ml flask equipped with a magnetic stirrer, 10 g of venlafaxine hydrochloride was dissolved in a mixture of 40 ml of ethyl acetate and 40 ml of water. Then, 4.8 ml of 28–30% aqueous ammonium hydroxide was added while stirring. The stirring was continued for 30 minutes and the layers were separated. The aqueous layer was extracted with 10 ml of ethyl acetate. The combined organic layers were washed with 20 ml brine and 20 ml of water. To the washed (not dried) organic layer was slowly added 5.0 g of 97% benzene sulfonic acid (hydrate) dissolved in 10 ml of ethyl acetate. After a few minutes, a white precipitate was formed. After stirring for 1 hour at 4° C., the crystals were isolated by filtration and dried overnight at 40° C. in vacuo. Isolated yield: 12.27 g (84.9%) venlafaxine besylate monohydrate Example 3A
Recrystallization of Venlafaxine Besylate Monohydrate In a 100 ml flask, equipped with a mechanical stirrer and a cooler, 1.0 g venlafaxine besylate monohydrate was dissolved under heating in 10 ml water while stirring. The hot clear solution was allowed to cool to room temperature overnight. After a few hours, the crystallization process started. After 18 hours, the crystals were isolated by filtration and dried over the weekend on a paper filter at room temperature and under atmospheric pressure. Isolated yield of venlafaxine besylate monohydrate was 0.73 g (73%). This was confirmed by Karl-Fischer method (4%, corresponding with 1 equivalent of water). Melting range 105–112° C.

Example 3B
Recrystallization of Venlafaxine Besylate Monohydrate

In a 100 ml flask equipped with a mechanical stirred and a cooler, 5.0 g of venlafaxine besylate monohydrate was dissolved under heating in 12 ml of 95% ethanol. The clear hot solution was allowed to cool to room temperature while stirring. The cold mixture was stirred for another 1 hour at room temperature. The crystals were isolated by filtration, washed with 5 ml of ethanol and dried overnight at reduced pressure. Isolated yield: 3.06 g. Water content 4.09% (K. Fischer). Melting range 85–112° C.; DSC peak 114.48° C.

Example 3C
Recrystallization of Venlafaxine Besylate Monohydrate from Acetone

In a 100 ml flask, equipped with a mechanical stirrer and cooler, 5.0 g of venlafaxine besylate monohydrate was dissolved under heating in 80 ml of acetone. The hot clear solution was allowed to cool to room temperature while stirring. The cold mixture was stirred for another 1 hour at room temperature. The crystals were isolated by filtration, washed with 20 ml of acetone and dried overnight at 40° C. in vacuo. Isolated yield: 4.183 g. NMR confirmed the structure. Water content 4.08% (Karl-Fischer). Melting range 85–114° C.; DSC peak: 114.21° C.

Example 3D 1.0 g of venlafaxine besylate monohydrate was dissolved in 17 ml of ethyl acetate at reflux. The solution was allowed to cool to room temperature and left at room temperature for about 30 minutes. The crystals were isolated by filtration and washed with ethyl acetate. The crystals were dried overnight in a vacuum oven at room temperature. Isolated yield: 880 mg (88%), water content corresponds to monohydrate; DSC peak at 115.22° C.

Example 3E 1.0 g of venlafaxine besylate monohydrate was dissolved in 3 ml of isopropanol at reflux. The solution was allowed to cool to room temperature and kept overnight at the same temperature. The crystals were isolated by filtration and washed with isopropanol. The crystals were dried for 22 hours in a vacuum oven at 40° C. The yield was 860 mg (86%). DSC peak: 115.03° C., water content corresponds to monohydrate.

Example 3F 1.0 g of venlafaxine besylate monohydrate was dissolved in 3 ml of ethanol at reflux. To the warm solution, 30 ml of cold n-heptane (0° C.) was added (initially dropwise, then in steps of 10 ml) and the mixture was cooled with ice. The suspension was stored at room temperature for 30 minutes, during which crystals appeared. The crystals were isolated by filtration and washed with n-heptane. The crystals were dried overnight in a vacuum oven at 40° C. The yield 850 mg (85%). DSC: melting endotherm at 114° C.; water content corresponds to the monohydrate.

Example 4A
Venlafaxine Besylate Anhydrate

In a 100 ml flask equipped with a stirring bar and a Dean-Stark apparatus, 3.03 g of venlafaxine besylate monohydrate was heated in 40 ml of toluene. The water was removed by azeotropic distillation and, after 4 hours, the clear solution was allowed to cool to room temperature under a nitrogen atmosphere. After removal of most of the toluene at reduced pressure, the obtained oily substance was stored under oil-pump vacuum for 15 hours to remove traces of toluene. A white foam was obtained which solidified after another 15 hours under vacuum. Water content (Karl-Fischer): 0.28%.

Storage of the product for 3 days at 40° C. and 75% relative humidity resulted in water uptake to a content of 4% of water (K. Fischer), corresponding to 1 equivalent of water.

Example 4B
Amorphous Venlafaxine Besylate 400 mg of venlafaxine besylate monohydrate was dissolved in 30 ml of water under heating. The hot solution was quench cooled to −78° C. and the frozen solution was freeze dried for about one day. The obtained solid was kept under vacuum for an additional day. White foamy amorphous venlafaxine besylate anhydrate was obtained. DSC: single melting peak at 120° C.

The product was exposed to air for 13 days. Visual recrystallization was observed. Karl-Fischer titration showed the presence of 1 equivalent of water. Melting endotherm by DSC at 114.85° C.

Example 4C
Less Hydrated Venlafaxine Besylate 1.0 g of venlafaxine besylate monohydrate was dissolved in 20 ml of ethyl acetate at reflux. The warm solution was dropwise added to 100 ml cold n-heptane (−74° C.) while stirring. The formed suspension was filtered cold over glass filter and washed with n-heptane. The obtained crystals were dried overnight in a vacuum oven at 40° C. The material is in a form of small white grains. Yield: 430 mg (43%).

DSC: Two overlapping peaks between 100–115° C. Karl-Fischer titration showed less than 0.5 molar equivalents of water.

Example 4D
Less hydrated Venlafaxine Besylate 1.0 g of venlafaxine besylate monohydrate was dissolved in 20 ml of ethyl acetate under reflux. The warm solution was quench cooled to −76° C. and kept at this temperature for 30 minutes. An opalescent emulsion or suspension was obtained which is filtratable through a glass filter. The filtrate slowly yields white flocks of solid material. The solid was filtered off on the same glass filter, washed with small amount of ethyl acetate and dried for 3 days in vacuum oven at room temperature. A white fluffy powder (490 mg) was obtained. DSC scan shows two endotherms between 85° C. and 115° C. Heating in the hot stage shows partial melting and recrystallization between 70–90° C., followed by second melting at 90–120° C. Karl Fischer titration shows 0.25 molar equivalents of water. When exposed to air for 13 days at room temperature, the DSC is comparable with venlafaxine besylate monohydrate and Karl-Fischer titration shows the presence of 1 molar equivalent of water.

Example 5
(−)-Isomer of Venlafaxine Besylate

In a 100 ml flask, equipped with a stirring bar, 2.0 g (+)-venlafaxine free base, obtained according to the procedure described in J. Med. Chem. 1990, 33 (10), 2899 ($[\alpha]_D$=28.2° (in 95% ethanol, c=1.07); mp=104–106° C.), was dissolved under heating in 4 ml acetone. Then, 1.30 g benzene sulfonic acid hydrate was added in one portion. The mixture was heated back into solution and the resulting clear solution was allowed to cool to room temperature. No crystallization occurred. Even after storage at 4° C. or −20° C., no crystallization was observed. Then, 5–10 ml diethyl ether was added. A small amount was taken out of the solution and was added to an ether layer in a test-tube. After scratching with a Pasteur pipette, a small amount of solid was obtained, which was used for seeding. This seeding initiated the crystallization. The thus formed crystals were isolated by filtration, washed with diethyl ether and were dried overnight at 40° C. in vacuum. Isolated yield was 2.346 g of fluffy white crystals. From the mother liquid, another 0.491 g was isolated.

Total yield: 90%. According to Karl-Fischer, no water present, corresponding with the anhydrous form. DSC peak at 137.08° C.; m.p. 133–135° C.; $[\alpha]_D$=−5.42° (c=2.01, methanol 99.5%).

Example 6
(+)-Isomer of Venlafaxine Besylate

In a 100 ml flask, equipped with a stirring bar, 4.0 g (−)-venlafaxine free base, obtained according to the procedure described in J. Med. Chem. 1990, 33 (10), 2899 ($[\alpha]_D$=−27.4° (in 95% ethanol, c=1.04); mp=104–106° C.), was dissolved under heating in 8 ml acetone. Then, 2.59 g benzene sulfonic acid hydrate was added in one portion. The mixture was heated back into solution and the resulting clear solution was allowed to cool to room temperature. No crystallization occurred. Even after storage at 4° C. or −20° C., no crystallization was observed. Then, 15–20 ml diethyl ether was added. A small amount was taken out of the solution and was added to an ether layer in a test-tube. After scratching with a Pasteur pipette, a small amount of solid was obtained, which was used for seeding. This seeding initiated the crystallization. The thus formed crystals were isolated by filtration, washed with diethyl ether and were dried overnight at 40° C. in vacuum. Isolated yield was 4.763 g of fluffy white crystals. From the mother liquid, another 0.844 g was isolated. Total yield: 89%. According to Karl-Fischer, no water present, corresponding with the anhydrous form. DSC peak at 137.20° C.; m.p. 134–136° C.; $[\alpha]_D$=+6.00° (c=2.00, methanol 99.5%).

Example 7
Synthesis of Venlafaxine Besylate

In a 100 ml flask, equipped with a stirring bar, 3.0 g of 1-[2-amino-1-(4-methoxyphenyl)ethyl]cyclohexanol was suspended in 28 ml of water. Then, 2.9 ml of 37% formaldehyde and 3.9 ml of formic acid were added successively. The reaction mixture was refluxed for 20 hours. After cooling to room temperature, the solvent was evaporated at reduced pressure on a water bath at 60° C., leaving a yellow/orange oil (approx. 5 g).

Then, 6 ml of water was added, followed by addition of 1.9 g of benzene sulfonic acid. The mixture was stirred and cooled by ice-bath. The separated crystals were isolated by filtration and washed with small amount of water, acetone and ether. The crystalline solid was dried overnight at 40° C. at reduced pressure. Isolated yield: 3.24 g. Water content (Karl-Fischer) 4.09%. m.p. 91–110° C. (melting range). HPLC purity: 97.8%.

Example 8
Water Solubility of Venlafaxine Salts 0.5 g of venlafaxine besylate was added to 10.0 ml of water and the resulting suspension stirred for 18 hours at room temperature. A 1 ml sample was withdrawn, filtered and the filtrate was freeze dried to yield about 26 mg. Thus, the venlafaxine besylate compound has a water solubility of about 26 mg/ml.

Example 9
Immediate Release Tablet 37.5 mg strength round 7 mm diameter tablets having a hardness of 60 N were made having the following composition:

| Ingredients | Mg/tablet | % |
|---|---|---|
| Venlafaxine besylate monohydrate | 61.3 | 40.87 |
| Microcrystalline cellulose (Avicel PH 102) | 60.00 | 40.00 |
| Lactose monohydrate | 23.62 | 15.74 |
| Sodium starch glycollate | 4.5 | 3.0 |
| Magnesium stearate | 0.58 | 0.39 |

Example 10
Extended Release Tablet

Tablet Composition Comprising Venlafaxine Besylate Composition of a Tablet:

| | |
|---|---|
| Venlafaxine besylate monohydrate | 244.72 mg |
| Hydroxypropylmethylcellulose (Methocel ™ K4M) | 244.72 mg |
| Magnesium stearate | 4.90 mg |

Modus Operandi:

Round biconvex tablets of 9 mm diameter/oval tablets of 16×8 mm size and having total mass of 494.34 mg were made by direct compression.

Dissolution rate (USP1, water, 37° C.) was determined by UV spectrophotometry and is expressed in % of the declared amount:

2 hrs 20.1%–21.9%
4 hrs 35.5%–37.1%
8 hrs 57.9%–60.3%
12 hrs 75.6%
24 hrs 106.0%

Example 11

The following tablets were made by direct compression:

| Ingredients | 37.5 mg/tablet | 75 mg/tablet | 150 mg/tablet |
|---|---|---|---|
| Venlafaxine besylate monohydrate | 61.3 | 122.6 | 244.72 |
| HPMC (Methocel K 4M EP) | 61.3 | 122.6 | 244.72 |
| Microcrystalline cellulose (Avicel PH 102) | 18.0 | 36.0 | — |
| Dibasic calcium phosphate anhydrous (Emcompress) | 8.0 | 16.0 | — |
| Magnesium stearate | 1.4 | 2.8 | 4.9 |

The 37.5 mg strength tablets were made as both round tablets (6 mm) and oval tablets (4×8 mm). The 75 mg strength tablets were made as round tablets (8 mm). The 150 mg strength was made as both round tablets (9 mm) and oval (16×8 mm).

Example 12

Small tablets were made having the following composition by compaction followed by compression.

| Ingredients | mg/tablet |
|---|---|
| Venlafaxine besylate monohydrate | 61.3 |
| HPMC (Methocel K 4M EP) | 61.3 |
| Microcrystalline cellulose (Avicel PH 102) | 18.0 |
| Dibasic calcium phosphate anhydrous (Emcompress) | 8.0 |
| Magnesium stearate | 1.4 |

The round tablets had a diameter of 6 mm. Three types of capsules were made from the tablets: a one tablet, a two tablet and a four tablet-containing capsule. The 37.5 mg, 75 mg, and 150 mg strength capsules all exhibited good extended release profile and are considered to be once daily capsules.

Example 13
Tablet Composition Comprising Venlafaxine Besylate Composition of a Tablet

| | | |
|---|---|---|
| Venlafaxine besylate | 61.30 mg | Active substance |
| Glyceryl behenate (Compritol ATO 888) | 10.00 mg | Fusible carrier |
| Anhydrous dicalcium phosphate | 27.70 mg | Filler |
| Magnesium stearate | 1.00 mg | Lubricant |
| Total weight | 100.00 mg | |

Ratio Venlafaxine besylate: Compritol 1:0.16

Modus operandi: Hot melt granulation followed by compression and coating

Hot Melt Granulation (High Shear Mixer)

Venlafaxine besylate and Compritol ATO 888 are added to the bowl of a high shear mixer and mixed for 5 minutes. Bowl temperature is increased by hot air and/or microwaves up to approximately 70° C. and a partially melted mass of Compritol ATO 888 and Venlafaxine besylate is obtained. Then, hot air and/or microwaves are stopped and cool water is passed through the jacket and inert gas through the partially melted mass to cool it. This solid product was a free flowing granulate Sieving The granulate was sieved to calibrate the size of the granulate.

Compression (Eccentric Compression Machine)

Once the granulate is obtained, the filler is added. In this case the filler is anhydrous dicalcium phosphate. This product is mixed for 15 minutes and then magnesium stearate is added and mixed for 5 minutes to obtain a tabletting mixture. This mixture is compressed into round biconvex tablets of 5 mm diameter.

Enteric Coating (Coating Machine)

These tablets are coated with an enteric film, Acryl-EZE®.

The tablets do not exhibit release in the gastric cavity and start releasing in a control-extended way when they leave the stomach. Dissolution rate (USP1, 2 hours in SGF pH 1.2 and 12 hours in SIF pH=6.8, 37° C.) was determined by UV spectrophotometry and is expressed in % of the declared amount.

| Hours | % dissolved | % dissolved preferred target ranges |
|---|---|---|
| 0 | 0 | |
| 1 | 0 | |
| 2 | 0 | <30% |
| 3 | 29.5 | |
| 4 | 40.6 | 30–55% |
| 8 | 64.1 | 55–80% |
| 12 | 77.8 | 65–90% |
| 24 | 101.1 | >80% |

Example 14

Tablet Composition Comprising Venlafaxine Besylate

Composition of a Tablet

| | | |
|---|---|---|
| Venlafaxine besylate | 61.30 mg | Active substance |
| Glyceryl behenate (Compritol ATO 888) | 18.39 mg | Fusible carrier |
| Lactose | 19.31 mg | Filler |
| Magnesium stearate | 1.00 mg | Lubricant |
| Total weight | 100.00 mg | |

Ratio Venlafaxine besylate: Compritol 1:0,30

Modus operandi: Hot melt granulation followed by compression and coating.

Hot Melt Granulation (High Shear Mixer)

Venlafaxine besylate and Compritol ATO 888 are added to the bowl of the high shear mixer and mixed for 5 minutes. Bowl temperature is increased by hot air and microwaves up to approximately 70° C. and a partially melted mass of Compritol ATO 888 and Venlafaxine besylate is obtained. Then, hot air and microwaves are stopped and cool water is passed through the jacket, the melted product is cooled. This solid product is a free flowing granulate.

Sieving

The granulate is sieved to calibrate the size of the particles.

Compression (Eccentric Compression Machine).

Once the granulate is obtained, the filler is added. In this case the filler is lactose. This product is mixed for 15 minutes and then magnesium stearate is added and mixed for 5 minutes.

This product is compressed in round biconvex tablets of 5 mm diameter.

Enteric Coating (Coating Machine)

These tablets are coated with an enteric film, Acryl-EZE.

Example 15

Tablet composition comprising venlafaxine besylate

| | | |
|---|---|---|
| Venlafaxine besylate | 61.30 mg | Active substance |
| Glyceryl behenate (Compritol ATO 888) | 10.00 mg | Fusible carrier |
| Magnesium stearate | 0.70 mg | Lubricant |
| Total weight | 72.00 mg | |

Ratio Venlafaxine besylate: Compritol 1:0,16

Modus operandi: Hot melt granulation followed by compression and coating

Hot Melt Granulation (High Shear Mixer)

Venlafaxine besylate and Compritol ATO 888 are added to the bowl of the high shear mixer and mixed for 5 minutes. Bowl temperature is increased by hot air and microwaves up to approximately 70° C. and a partially melted mass of Compritol ATO 888 and Venlafaxine besylate is obtained. Then, hot air and microwaves are stopped and cool water is passed through the jacket, the melted product is cooled. This solid product is a granulate.

Sieving

This granulate obtained is sieved in order to calibrate the size particle.

Compression (Eccentric Compression Machine)

Magnesium stearate is added to the granulate and mixed for 5 minutes. This product is compressed in round biconvex tablets of 5 mm diameter.

Enteric Coating (Coating machine)

These tablets are coated with an enteric film made of Acryl-EZE®.

Dissolution rate (USP1, 2 hours in SGF pH 1.2 and 12 hours in SIF pH 6.8, 37° C.) was determined by UV spectrophotometry and is expressed in % of the declared amount.

| Hours | % dissolved | % dissolved preferred target ranges |
|---|---|---|
| 0 | 0 | |
| 1 | 0 | |
| 2 | 0 | <30% |
| 4 | 43.7 | 30–55% |
| 8 | 72.1 | 55–80% |
| 12 | 87.3 | 65–90% |
| 24 | 102.7 | >80% |

Example 16

Tablet Composition Comprising Venlafaxine Besylate

| | | |
|---|---|---|
| Venlafaxine besylate | 61.30 mg | Active substance |
| Glyceryl behenate (Compritol ATO 888) | 10.00 mg | Fusible carrier |
| Anhydrous dicalcium phosphate | 12.85 mg | Filler |
| Magnesium stearate | 0.85 mg | Lubricant |
| Total weight | 85.00 mg | |

Ratio Venlafaxine besylate: Compritol 1:0,16

Modus operandi: Hot melt granulation followed by compression and coating

Hot Melt Granulation (High Shear Mixer)

Venlafaxine besylate and Compritol ATO 888 are added to the bowl of the high shear mixer and mixed for 5 minutes. Bowl temperature is increased by hot air and microwaves up to approximately 70° C. and a partially melted mass of Compritol ATO 888 and Venlafaxine besylate is obtained. Then, hot air and microwaves are stopped and cool water is passed through the jacket, the melted product is cooled. This solid product is a granulate.

Sieving

This granulate obtained is sieved in order to calibrate the size particle.

Compression (Eccentric Compression Machine)

Anhydrous dicalcium phosphate is mixed for 15 minutes and then magnesium stearate is added and mixed for 5 minutes. This product is compressed in round biconvex tablets of 5 mm diameter.

Enteric Coating (Coating Machine)

These tablets are coated with an enteric film made from Acryl-EZE®. Dissolution rate (USP1, 2 hours in SGF pH 1.2 and 12 hours in SIF pH 6.8, 37° C.) was determined by UV spectrophotometry and is expressed in % of the declared amount.

| Hours | % dissolved | % dissolved preferred target ranges |
| --- | --- | --- |
| 0 | 0 | |
| 1 | 0 | |
| 2 | 0 | <30% |
| 4 | 41.3 | 30–55% |
| 8 | 70.4 | 55–80% |
| 12 | 86.3 | 65–90% |
| 24 | 104.8 | >80% |

Example 17
Tablet composition comprising venlafaxine besylate (Cutina+Compritol as waxes)

| | | |
| --- | --- | --- |
| Venlafaxine besylate | 61.30 mg | Active substance |
| Glyceryl behenate (Compritol ATO 888) | 9.81 mg | Fusible carrier |
| Hydrogenated Castor Oil (Cutina HR) | 6.13 mg | Fusible carrier |
| Magnesium stearate | 0.78 mg | Lubricant |
| Total weight | 78.02 mg | |

Ratio Venlafaxine besylate: Waxes (Compritol+Cutina) 1:0.26

Modus operandi: Hot melt granulation followed by compression.

Hot Melt Granulation (High Shear Mixer)

Venlafaxine besylate, Compritol ATO 888 and Cutina HR are added to the bowl of the high shear mixer and mixed for 5 minutes. Bowl temperature is increased by hot air and microwaves up to approximately 70° C. and a partially melted mass of Compritol ATO 888, Cutina HR and Venlafaxine besylate is obtained. Then, hot air and microwaves are stopped and cool water is passed through the jacket, the melted product is cooled. This solid product is a granulate.

Sieving

This granulate obtained is sieved in order to calibrate the size particle.

Compression (Eccentric Compression Machine)

Magnesium stearate is added to the granulate and mixed for 5 minutes. This product is compressed in round biconvex tablets of 5 mm diameter.

Dissolution rate (USP 1, 24 hours in SIF pH 6.8, 37.5° C.) was determined by UV spectrophotometry and is expressed in % of the declared amount.

| Hours | % dissolved | % dissolved preferred target range |
| --- | --- | --- |
| 2 | 33.6 | <30% |
| 4 | 47.0 | 30–55% |
| 8 | 63.9 | 55–80% |
| 12 | 75.1 | 65–90% |
| 24 | 95.7 | >80% |

Example 18
Lipophilic Matrix-based Tablets (37.5 mg Venlafaxine) by Direct Compression Composition of Tablet

| | | |
| --- | --- | --- |
| Venlafaxine besylate | 61.30 mg | Active substance |
| Glyceryl behenate (Compritol ATO 888) | 12.26 mg | Fusible carrier |
| Magnesium stearate | 0.74 mg | Lubricant |
| Total weight | 74.30 mg | |

Ratio Venlafaxine besylate: Compritol 1:0,20

Modus operandi: Direct compression

Compression (Eccentric Compression Machine)

Dissolution rate (USP1, 2 hours in SGF pH 1.2 and 12 hours in SIF pH 6.8, 37° C.) was determined by UV spectrophotometry and is expressed in % of the declared amount.

| Hours | % dissolved |
| --- | --- |
| 0 hrs | 0 |
| 1 hrs | 50.7% |
| 2 hrs | 73.0% |

Example 19
Tablet Composition Comprising Venlafaxine Besylate

| | | |
| --- | --- | --- |
| Venlafaxine besylate | 61.30 mg | Active substance |
| Glyceryl behenate (Compritol ATO 888) | 10.00 mg | Fusible carrier |
| Magnesium stearate | 0.70 mg | Lubricant |
| Total weight | 72.00 mg | |

Ratio Venlafaxine besylate: Compritol 1:0.16

Modus operandi: Hot melt granulation followed by compression and coating

Hot Melt Granulation (High Shear Mixer)

Venlafaxine besylate and Compritol ATO 888 are added to the bowl of the high shear mixer and mixed for 5 minutes. Bowl temperature is increased by hot air and microwaves up to approximately 70° C. and a partially melted mass of Compritol ATO 888 and Venlafaxine besylate is obtained. Then, hot air and microwaves are stopped and cool water is passed through the jacket, the melted product is cooled. This solid product is a granulate.

Sieving

This granulate obtained is sieved in order to calibrate the size particle.

Compression (Eccentric Compression Machine)

Magnesium stearate is added to the granulate and mixed for 5 minutes. This product is compressed in round biconvex tablets of 5 mm diameter.

Enteric Coating (Coating machine)

These tablets are coated with an enteric film made of Acryl-EZE® containing a 20% of sucrose (according to solid Acryl-EZE® content) as pore forming agent.

Dissolution rate (USP1, 2 hours in SGF pH 1.2 and 12 hours in SIF pH 6.8, 37° C.) was determined by UV spectrophotometry and is expressed in % of the declared amount.

| Hours | % dissolved | % dissolved preferred target range |
|---|---|---|
| 0 | 0 | |
| 1 | 3.6 | |
| 2 | 7.8 | <30% |
| 4 | 42.0 | 30–55% |
| 8 | 79.1 | 55–80% |
| 12 | 91.3 | 65–90% |

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A venlafaxine besylate compound.
2. The venlafaxine besylate compound according to claim 1, which is crystalline venlafaxine besylate.
3. The venlafaxine besylate compound according to claim 1, wherein said venlafaxine is (+/−)-venlafaxine.
4. The venlafaxine besylate compound according to claim 2, which is crystalline venlafaxine besylate monohydrate.
5. The venlafaxine besylate compound according to claim 4, which is crystalline (+/−)-venlafaxine besylate monohydrate.
6. The venlafaxine besylate compound according to claim 2, which is crystalline venlafaxine besylate anhydrate.
7. The venlafaxine besylate compound according to claim 1, wherein said venlafaxine is pure or substantially pure (+) or (−) venlafaxine enantiomer.
8. A pharmaceutical composition comprising a venlafaxine besylate compound and at least one pharmaceutically acceptable excipient.
9. The composition according to claim 8, wherein said at least one excipient is selected from the group consisting of polymers, waxes, calcium phosphates, and sugars.
10. The composition according to claim 9, wherein said at least one excipient is selected from the group consisting of HPMC, microcrystalline cellulose, and calcium phosphates.
11. The composition according to claim 10, which further comprises a lubricant.
12. The composition according to claim 9, wherein said at least one excipient is selected from the group consisting of hydrogenated castor oil, glyceryl behenate, glycerylpalmito stearate, and saturated polyglycolyzed glycerate.
13. The composition according to claim 8, wherein said composition is in the form of granules, pellets, or a powder blend.
14. The composition according to claim 8, wherein said composition is in the form of a tablet.
15. The composition according to claim 8, wherein said composition is a unit dosage form and said venlafaxine besylate is contained in an amount between 30 mg and 300 mg.
16. The composition according to claim 8, wherein said composition is an extended release composition.
17. The composition according to claim 16, wherein said composition has a dissolution profile such that less than 30% of said venlafaxine besylate is released from said composition in 2 hours using either purified water or SGF at 37° C. with stirring at 100 r.p.m. in a basket apparatus.
18. The composition according to claim 17, wherein said composition has a release profile that satisfies the following:

| Time (hours) | Average % venlafaxine besylate released |
|---|---|
| 2 | <30 |
| 4 | 30–55 |
| 8 | 55–80 |
| 12 | 65–90 |
| 24 | >80 | using USP Apparatus 1 (basket) at 100 rpm in purified water at 37° C.

19. The composition according to claim 16, wherein said composition is a once daily dose tablet.
20. The composition according to claim 16, wherein said composition is a tablet and said at least one excipient is a matrix material.
21. The composition according to claim 20, wherein said matrix material is a hydrophilic, lipophilic or biodegradable matrix material.
22. The composition according to claim 21, wherein said tablet is a hydrogel tablet.
23. The composition according to claim 21, wherein said tablet comprises hydroxypropylmethyl cellulose and venlafaxine besylate.
24. The composition according to claim 23, which further comprises a calcium phosphate, microcrystalline cellulose, or a lubricant.
25. The composition according to claim 23, wherein said tablet is a once daily dose tablet.
26. The composition according to claim 21, wherein said matrix material is a lipophilic matrix material.
27. The composition according to claim 26, wherein said matrix material is selected from the group consisting of glyceryl palmitostearate, glyceryl behenate, and hydrogenated castor oil.
28. The composition according to claim 27, wherein said tablet further comprises a calcium phosphate or a lubricant.
29. The composition according to claim 26, wherein said tablet is a once daily dose tablet.
30. The composition according to claim 16, wherein said composition is in the form of pellets.
31. The composition according to claim 30, wherein said pellets have a dissolution profile that satisfies the following criteria:

| Time (hours) | Average % venlafaxine besylate released |
|---|---|
| 2 | <30 |
| 4 | 30–55 |
| 8 | 55–80 |
| 12 | 65–90 |
| 24 | >80 | using USP Apparatus 1 (basket) at 100 rpm in purified water at 37° C.

32. The composition according to any one of claims 8–31, wherein said venlafaxine besylate is (+/−)-venlafaxine besylate monohydrate.
33. A method for treating a venlafaxine-treatable disease or condition, which comprises administering to a patient in need thereof an effective amount of a venlafaxine besylate compound.
34. The method according to claim 33, wherein said venlafaxine besylate compound is administered in the form of a tablet.

35. The method according to claim 34, wherein said patient suffers from depression and said effective amount of venlafaxine besylate is an antidepressant amount.

36. The method according to claim 33, wherein said venlafaxine besylate compound is administered once daily.

37. The method according to claim 36, wherein said venlafaxine besylate compound is administered orally in the form of one or two tablets once daily.

38. A process, which comprises:
mixing venlafaxine besylate and a molten fusible carrier to form a partially melted mass; and
cooling said partially melted mass to form a solidified product.

39. The process according to claim 38, wherein said solidified product is in the form of granules or pellets.

40. The process according to claim 39, which further comprises milling said solidified product to form granules.

41. The process according to claim 38, which further comprises combining, prior to said mixing step, said fusible carrier in a non-molten state with said venlafaxine besylate and heating to render said fusible carrier molten.

42. The process according to claim 38, wherein said fusible carrier is a lipophilic matrix material.

43. The process according to claim 42, wherein said fusible carrier is a wax.

44. The process according to claim 38, wherein said mixing step further includes mixing at least excipient selected from the group consisting of calcium phosphates, microcrystalline cellulose, and lactose.

45. The process according to claim 44, which further comprises mixing said solidified product, optionally after milling, with a lubricant to form a tabletting mixture and forming a tablet from said tabletting mixture.

46. The process according to claim 38, which further comprises mixing said solidified product, optionally after milling, with a lubricant and at least one excipient selected from the group consisting of calcium phosphates, microcrystalline cellulose, and lactose.

47. The process according to claim 38, which further comprises converting said solidified product into a tablet.

48. The process according to claim 47, wherein said tablet is an extended release tablet.

49. The process according to claim 48, wherein said tablet has a release profile that satisfies the following:

| Time (hours) | Average % venlafaxine besylate released |
|---|---|
| 2 | <30 |
| 4 | 30–55 |
| 8 | 55–80 |
| 12 | 65–90 |
| 24 | >80 | using USP Apparatus 1 (basket) at 100 rpm in purified water at 37° C.

* * * * *